United States Patent [19]

Kappe et al.

[11] 4,055,752
[45] Oct. 25, 1977

[54] METHOD AND APPARATUS FOR THE DETERMINATION OF ENZYME ACTIVITY

[75] Inventors: Walter Kappe, Oberkochen; Götz-Reinhard Lampe, Heidenheim; Harald Neuer, Oberkochen, all of Germany

[73] Assignee: Carl Zeiss-Stiftung, Oberkochen, Wurttemberg, Germany

[21] Appl. No.: 546,144

[22] Filed: Jan. 31, 1975

[30] Foreign Application Priority Data

Feb. 7, 1974 Germany .............................. 2405810

[51] Int. Cl.² ........................................... G06F 15/42
[52] U.S. Cl. .................................... 364/551; 356/215; 23/230 B; 195/103.5 R; 364/570
[58] Field of Search ........................ 235/151.35, 151.3; 356/213, 205, 103, 147; 23/230 R, 230 B; 195/103.5 R; 250/218; 340/172.5

[56] References Cited

U.S. PATENT DOCUMENTS

| | | | |
|---|---|---|---|
| 3,656,116 | 4/1972 | Jansen, Jr. .......................... | 340/172.5 |
| 3,725,204 | 4/1973 | Marshall, Jr. et al .... | 195/103.5 R X |
| 3,748,044 | 7/1973 | Liston .......................... | 235/151.35 X |
| 3,760,171 | 9/1973 | Wang et al. .................. | 340/172.5 X |
| 3,775,595 | 11/1973 | Rosse et al. ................. | 235/151.35 X |
| 3,832,532 | 8/1974 | Praglin et al. .............. | 235/151.35 X |
| 3,847,486 | 11/1974 | McCabe .............................. | 356/39 X |
| 3,878,378 | 4/1975 | Johnson et al. ................. | 235/151.35 |
| 3,881,992 | 5/1975 | Ralston .......................... | 195/103.5 R |

Primary Examiner—Edward J. Wise

[57] ABSTRACT

Enzyme activity for a given sample is automatically determined by measuring light-extinction, at each of a succession of "points" in time and involving a plurality of measurements at each such time. At each of these "points" in time, the several individual measurements are made within a period of time which is brief as compared with the period of time between successive measurement points, and mean value and standard deviation are calculated from these individual measurements. A regression curve is drawn through the measurement points thus obtained, the enzyme activity being determined from the slope thereof at a predetermined time. A total measurement error is also calculated at the same time.

17 Claims, 4 Drawing Figures

METHOD AND APPARATUS FOR THE DETERMINATION OF ENZYME ACTIVITY

The present invention relates to a method and apparatus for the determination of enzyme activity, in which a plurality of measurement points succeed each other at predetermined time intervals, for successive occasions in which the sample is subjected to a light-extinction measurement.

The determination of enzyme activity has been of great importance for years, particularly in clinical chemistry, since it makes possible a very early diagnosis of various diseases as well as a check-up of the course and treatment thereof.

The activity of an enzyme is established by the initial velocity of an enzyme-catalyzed reaction under given conditions and, therefore, by the decrease in substrate concentration with reaction time. In order to measure the enzyme activity, therefore, the substrate concentration must be determined at different reaction times. This can be done particularly rapidly and simply by extinction measurement if a light-absorbing substance is consumed or produced during the reaction. Alternatively, an indicator reaction is used in which a product of the actual test reaction is consumed with the formation of a light-absorbing substance; in such case, a preliminary reaction is first allowed to take place, and the test reaction is then started after a given period of time, by the addition of a starting reagent.

In order to maintain, within feasible limits, the cost of the apparatus for determining enzyme activity, one is generally restricted to (a) measuring the extinction value at precisely defined time intervals and (b) fitting a straight line to the measurement values thus determined, the slope of said line being proportional to the activity sought.

A few minutes are required for examination of each sample. Thus, it is a general practice to use a photometer to make several concurrent determinations, as by bringing, e.g., six different samples sequentially indexed, one after the other, into the path of the light-source beam, by means of an automatic cell arrangement, and by recording the extinction values. The measured values for different samples are thus interlaced with each other, and graphical techniques can facilitate their interpretation. However, each procedure requires particular care, is not free of errors (which are difficult to define), and requires a relatively long period of time.

For some time, there have been available on the market fixed-program digital computers which make it unnecessary for an operator to evaluate each recording. In this connection, several successive measurement cycles are carried out at given time intervals, several samples being brought successively into the path of the beam during each cycle, and a measurement value is determined for each sample. The computer then draws a straight line through the measured values of each sample, in such a manner that the deviations are as small as possible, and the enzyme activities of the individual samples are determined from the slope of this line. As indications of error, the computer provides either the maximum deviations of the measured values from the straight line or the mean deviation. Such a computer will also yield a digital output to indicate calculated enzyme activity, interpolated for a point in time between two successive measurement points.

Such known methods of evaluation have the fundamental disadvantage that they presuppose a linear relationship between changes in extinction and time. However, for the case of large values of enzyme activity, such as are present in pathological serums, for instance, this linear relationship is satisfied only at the start of each period of investigation. Therefore, if one calculates enzyme activity from the measured values for the entire period of examination, too low a value is obtained; on the other hand, if such activity is calculated only from the first-measured values, then the lack of percision is too great as a result of the measurement errors which are bound to occur. Such errors in measurement are of major importance since only relatively small changes in extincton occur during the entire time of the examination.

In the previous methods of evaluation, it is furthermore assumed thatthe individual measurement values obtained from the photometer are correct. However, this is an unreliable assumption, since photometric measurements are subject to uncertainty, due to noise or variations in the operating parameters. Since only relatively few — in general, five to seven — measurement points of each sample are plotted due to considerations of time, it is to be expected (pursuant to the rules of statistics) that, for an appreciable (i.e., non-negligible) number of samples, the predominant number of the measurement points will be so shifted in random fashion that too small or too large an activity is indicated.

Another defect of the previously known methods of measuring a plurality of samples with a cell-changing device resides in the factthat the individual samples have characteristic absorptions which differ greatly from each other. Samples having a high characteristic absorption are therefore measured at high extinction values although in principle only the change in extinction is of interest; a higher photometric precision would be obtained if the amplification of the photometer were increased, but this could frustrate measurements in case of a sample having a lower characteristic absorption, since samples of low characteristic absorption could lie outside the photometric measurement range.

All the apparatus for determining enzyme activity known up to the present time requires well trained operating personnel since it is necessary to effect adjustments of the apparatus, and such adjustments require much knowledge as to the manner of operation of the apparatus.

It is, accordingly, an object of the invention to provide an improved method and apparatus avoiding or substantially reducing above-noted difficulties or deficiencies of past practice.

It is a specific object to provide a method of determining enzyme activity, with dependable value determinations and with dependable indication of error.

Another specific object is to meet the above objects with a method and apparatus, even for the higher values of enzyme activity.

A general object is to meet said objects with less-expensive apparatus, which is relatively simple and automatic as to both measurement and evaluation processes, and which lends itself to reliable use by relatively unskilled operator personnel.

The invention contemplates an improved method for determining enzyme activity for a given sample, in which at predetermined time intervals, several measurement points (in general, five to seven) are obtained in succession by measuring the extinction of the sample and in which, according to this method said measurement points are obtained under automatic control, in such manner that at each point several individual measurements are made within a period of time which is brief as compared with the period of time between successive measurement points, and in which further (a) the mean value and standard deviation are calculated from these individual measurements and (b) a regression curve is drawn through the measurement points thus obtained, the enzyme activity being determined from the slope thereof at a predetermined time; a total measurement error is determined from the deviation of said regression curve from the measurement points, the standard deviations and the local curvature of the regression curve.

Thus, in the new method, each measurement point is obtained from a plurality of individual measurements succeeding each other at short time intervals and represents the mean value of these individual measurements. This technique precludes such random measurement errors as may occur in particular individual measurements. Determination of the standard deviation provides a measure for the dependability of the measurement point, calculated as mean value.

A regression curve is now drawn through the measurement points thus obtained, it being characteristically and therefore well represented by a oolynomial of the second degree. The regression curve is drawn through the measurement points in such a manner that the sum of the squares of the deviations in the individual measurement points is as small as possible. From the slope of the regression curve, at a predetermined point in time, the enzyme activity is then determined, an overall measurement error being determined at the same time from the error in fit of the curve, i.e., by comparing the standard deviations of the individual measurements, to the curvature of the regression curve. This overall measurement error constitutes an objective value and provides the person carrying out the measurement with a clear indication as to the accuracy with which the enzyme activity has been determined.

As already mentioned, in the new method, the regression curve is advantageously represented by a polynomial of the second degree. Such a polynomial is of the general form $E(t) = a_0 + a_1 t + a_2 t^2$ and has an additional term as compared with the straight-line relationship of prior techniques; the additional term effects a correction for $a_2 \neq 0$, i.e., when the test reaction does not proceed linearly during the entire period of measurement and thus provides a better fit of the regression curve to the measurement points.

Further in accordance with the invention, for the measurement of enzyme activity of a plurality of samples arranged in different cells, these cells are brought in succession into the measurement position in successive cycles, and an optimum photometric amplification is determined during the first measurement cycle for each sample, the amplification value being then set and stored. In succeeding measurement cycles, the stored amplification value is automatically set for each sample.

The amplification for each sample is so selected that measurement is effected with due consideration of the possible changes in he region most favorable photometrically, which lies for instance between the extinction values of 0 and 0.4. Each sample is measured precisely at the optimum amplification value corresponding to it without the operator having to change the adjustment of the apparatus. This feature of the invention is thus seen to provide greatly enhanced accuracy of measurement, particularly since each measurement point is obtained as the mean value of extinction values which are measured rapidly one after the other.

The method of the invention is particularly advantageous when the start of each succession of measurements is controlled by a clock signal, repeated precisely at the end of a predetermined time interval. This feature assures that, regardless of any influences which may be caused, for instance, by the cell-changing device, a measurement is always performed on each given sample after a precisely predetermined period of time, for instance in each case after precisely 30 seconds.

The clock signal is preferably produced by means of a real-time clock, but this clock can be replaced by snychronous motors or by other known devices.

In the new method, a photometer is ready for measurement only a predetermined period of time after it has been connected, in order to avoid difficulties as a result of starting-up effects.

The apparatus in accordance with the invention consists of a photometer equipped with an analog-digital converter for the measured value, the photometer being so combined with a freely programmable computer that all measurement processes of the photometer are controlled by the computer, and the computer carries out all arithmetic operations for the determination of the enzyme activity sought.

The free programmability of the computer provides the advantage that it is not necessary to establish in advance the final form of program for the obtaining and evaluation of the measurement values. Rather, the use of this computer makes it possible to effect, at low cost and rapidly, continuous adaptation to different tasks and to advances in the state of the analytical arts.

The invention will be explained below with reference to the accompanying drawings, in which.

Figure 4:
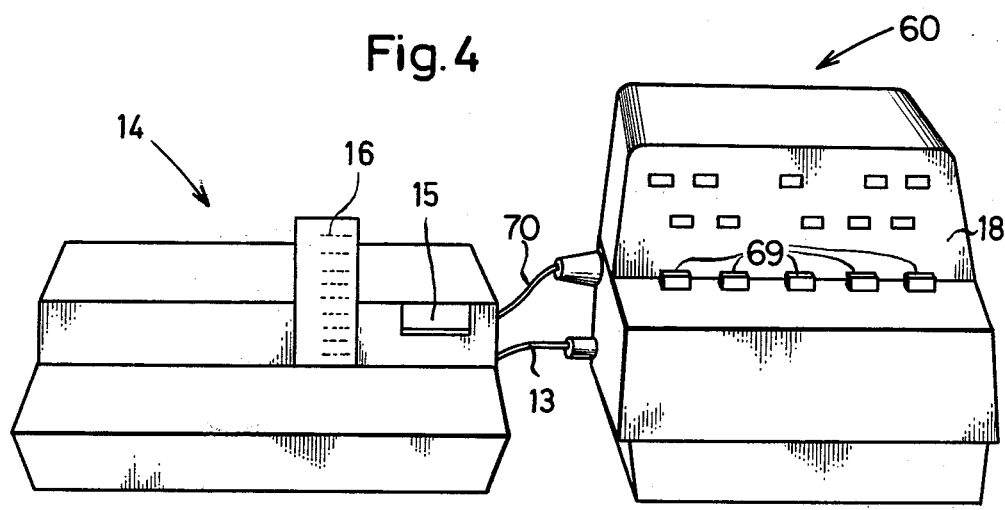
FIG. 4 shows an embodiment of an apparatus for carrying out the method of the invention.
Figure 2:
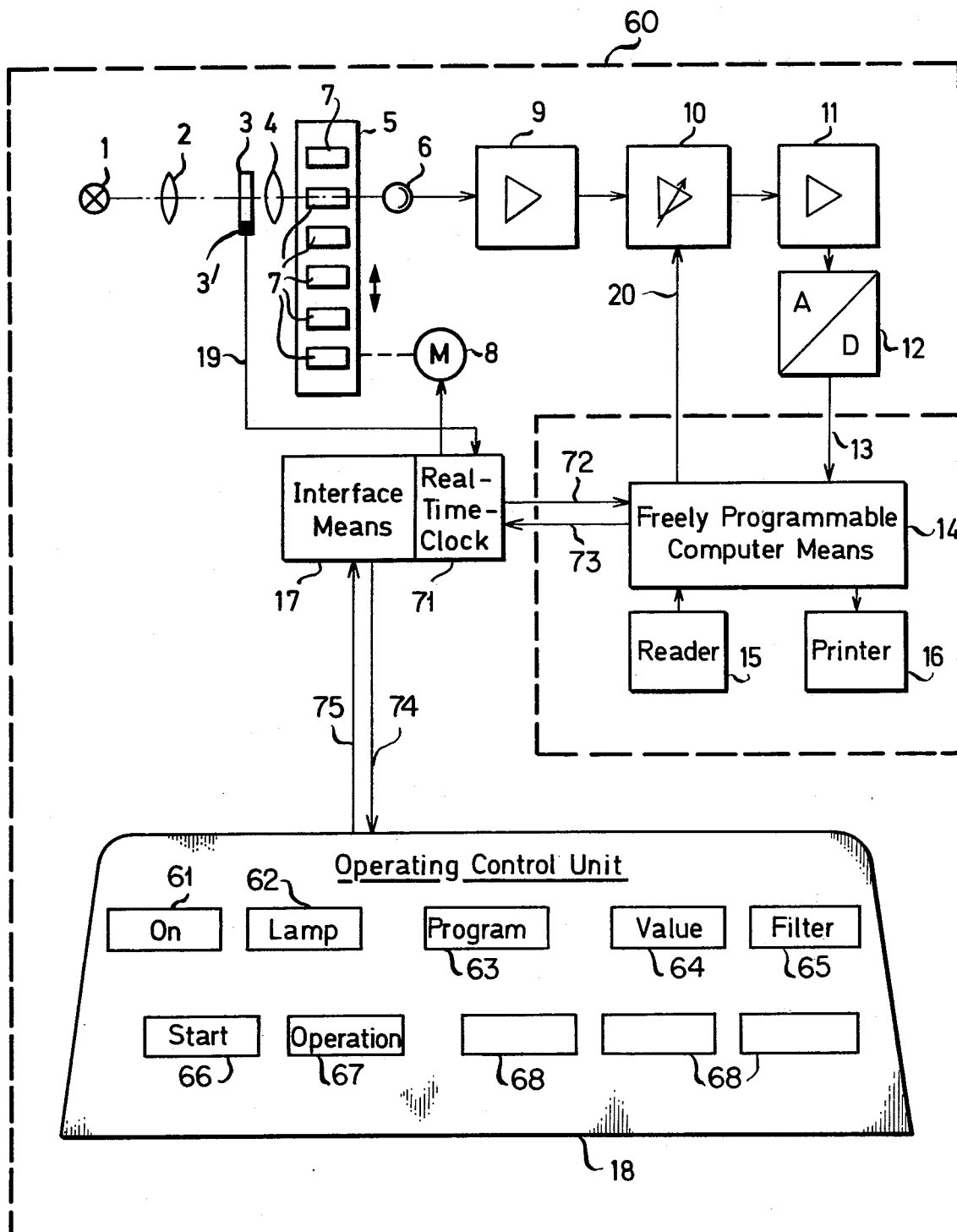
FIG. 2 is a block diagram of one embodiment of an apparatus for carrying out the method of the invention.

In the apparatus of FIG. 4, a single-beam photometer unit 60 is used, since the long time-constancy of good single-beam photometers is sufficient for the measurement of enzyme activity. In principle, however, double-beam photometers can also readily be used. This photometer unit is connected via cables 13 and 70 with a computer unit 14, shown as a small desk computer. This computer is freely programmable by inserting a corresponding magnetic card into the reading device 15. The results of the measurement are printed onto a paper strip by means of a printer The photometer unit 60 of FIG. 4 is shown in FIG. 2 to comprise a light source 1 which may be, for instance, a mercury vapor lamp. Light emerging from source 1 passes through a condenser 2, a filter 3, and a lens 4; it then passes through a sample space in which a cell-changing device 5 is movable (as suggested by a double arrow in FIG. 2) and finally falls on a receiver 6.

In the embodiment shown, the cell-changing device 5 comprises a frame for six cells 7, the same being transversely movable through the sample-supporting space by drive means 8.

The output signal of receiver 6 is amplified in a preamplifier 9 and then passes through an amplifier of adjustable amplification 10; it is finally amplified in an output amplifier 11 and passes to the input of an analog-digital converter 12. The latter converts the signal into a digital signal and feeds it via a line 13 to a freely programmable computer 14. The program input for the computer 14 takes place at 15 via a reading device, for instance a magnetic card or magnetic tape reader. With the computer 14 there is also connected a printer 16 which prints out the results.

The computer 14 is connected via interface means 17 with an operating or master control unit 18 which as is shown in FIG. 4 is part of the photometer unit 60 and contains various luminous-headed push buttons 61 to 68 but does not contain any read-out or indicating instrument.

As shown in FIG. 4, the photometer unit 60 contains several recesses in which filter casings 69 are inserted. For the measurement, one of the filters is selected by inserting the corresponding filter casing 69 into the middle recess. Thereby the selected filter 3 is inserted into the beam path as shown in FIG. 2. Along the side part of each filter casing are codings corresponding to the transmission wavelength characteristic of the particular filter; such codings may be indicated by depressions. These code numbers are read by micro-switches (suggested at the heavy square 3′ in FIG. 2), and the corresponding information is fed via a line 19 to the interface 17 and the computer 14.

The filter designation 3 will be understood to include optional use of a monochromator having a digital output for the instantaneous measurement-wavelength setting thereof.

The interface means 17 contains a real-time-clock 71 which, inter alia, assures a precisely fixed time between successive enzyme-activity measurements. For this purpose, clock pulses are fed to the computer 14 via line 72, causing the program contained in the computer to operate in synchronism with these pulses.

Figure 3:
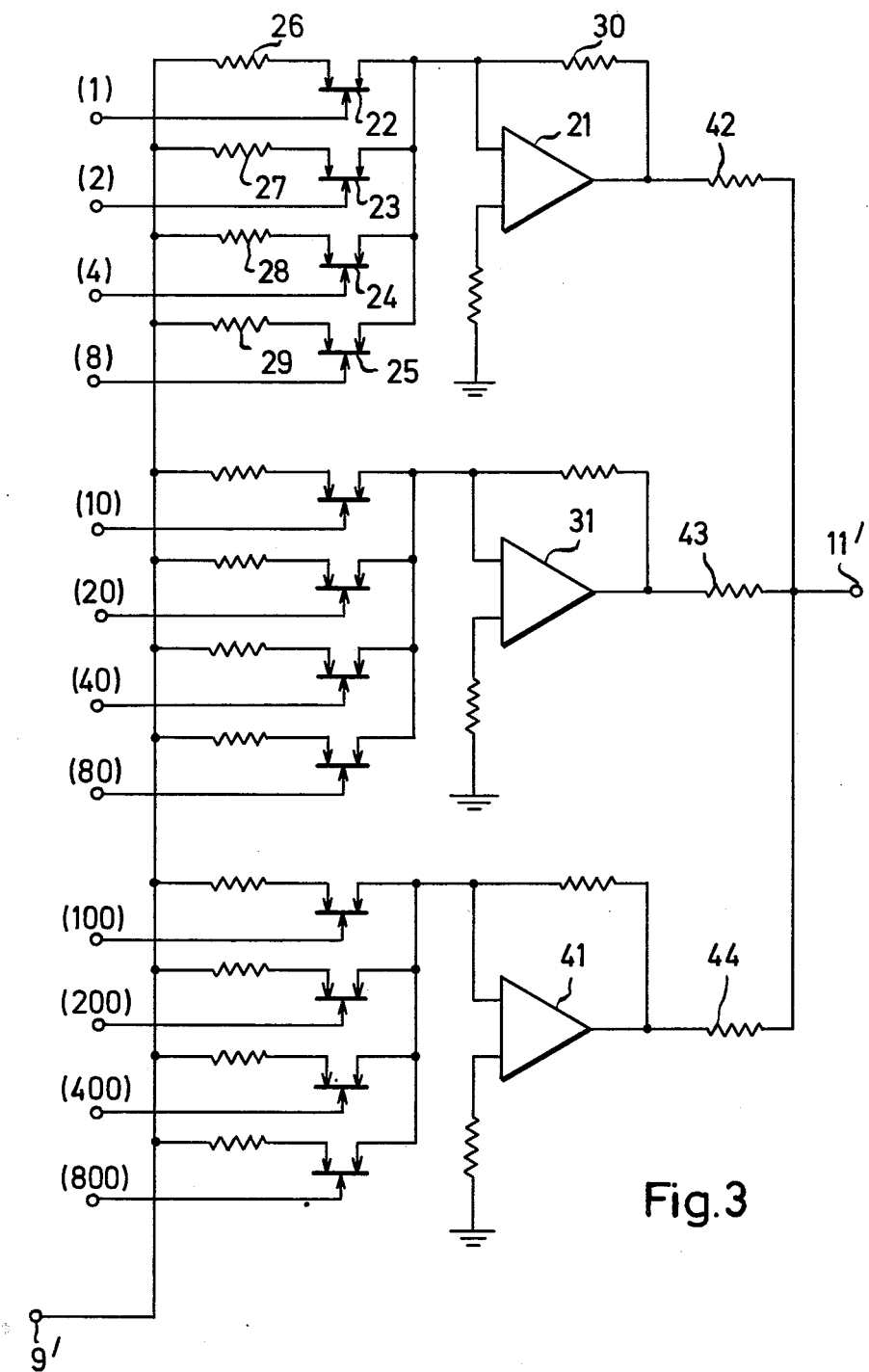
FIG. 3 is a circuit diagram for an amplification regulator used in the apparatus of FIG. 2.

FIG. 3 shows the circuit of the variable amplifier 10 of FIG. 2. It contains three operational amplifiers 21, 31, 41, all of which have similar connections so that detailed explanation of the operational amplifier 21 will suffice. One input of operational amplifier 21 is connected with four field-effect transistors 22, 23, 24, 25 and four resistors 26, 27, 28, 29. Each of the four field-effect transistors has an input, which inuts are designated corresponding to the respective digits of a four-digit binary code, with decimal-equivalent numbers placed in parentheses. Various actuations of these inputs single or in combination, will be understood to be controlled via the schematic line 20 from computer 14 (FIG. 2).

Amplification of the operational amplifier 21 is changed in the ratio 1:2:4:8 by the resistors 26–29, in the context of a feedback resistor 30; in this way, the amplification factors 0, 1, 2, . . . 15 can be set. An output resistor 42, in combination with a fofllowing operational amplifier (not shown) assures that the output voltage of the first circuit block (described in conjunction with amplifier 21) accounts for the "ones" ("units") position in the code used; this will be recognized for consistency with the inut designations employed for the respective transistors 22 to 25 serving amplifier 21. In similar fashion, the "tens" position is characterized by a second circuit block containing the operational amplifier 31, while the "hundreds" position is designated by the third circuit block containing the operational amplifier 41. The output resistors 44, 43, 42 have a ratio of their resistances of 1:10:100.

The manner of operation of the apparatus shown in FIG. 4 is as follows. First of all a filter 3 is selected by inserting its casing 69 into the middle recess of the photometer unit 60. Then the push button 61 is pressed thereby igniting the lamp of light source 1. After ignition of this lamp, push button 62 lights up. At the same time, a clock contained in photometer unit 60 is started. This clock, after a predetermined start-up time of say eight minutes, effects lighting up of push button 63, signalling that the apparatus is ready to start. Next, a magnetic card containing the computer program is inserted into reader 15 and by pressing push button 63 the program is read into the computer 14 and started. The program first effects the storing of a certain digital constant (a multiplication factor) in a storage of the computer 14. When this is effected, a lighting up of push button 64 is effected via lines 73 and 74. The program also contains the code number of the correct filter 3; in the next step, it effects a comparison between this code number and that delivered via lines 19, 72, and if said two numbers are not the same, the program comes to a stop and push button 65 lights up. The operator is thus alerted to correct the filter and as soon as the compared code numbers are the same, the program starts again and push button 66 lights up.

Pressing push button 66 now starts the measurement of the enzyme activity of the samples contained in cells 7. This measurement is effected in the following manner.

First, controlled by the program of the computer 14 via line 73 and interface 17, motor 8 is started and moves the first of the cells 7 into measurement position. At the same time the amplification factor of amplifier 10 is set at its lowest value. Now, the computer 14 calculates the optimal amplification factor. This digital factor (a) triggers via line 20 (contained in cable 70 of FIG. 4) the field-effect transistors of the circuit shown in FIG. 3 thus setting amplifier 10 to the optimal amplification factor, and (b) is stored in a storage of computer 14.

Having set amplifier 10 to its optimal gain, and under control by the computer program, several (for instance, ten) measurement values are now obtained in rapid sequence and are fed via line 13 to computer 14. This computer calculates the mean value and the standard deviation of said measurement values and stores these calculated values. The calculated mean value is used as a measurement point, designated 45 in FIG. 1, while the calculated standard deviation is indicated at 46.

After the first measurement of cell one is effected, the computer program comes to a stop. Via real-time-clock 71, it is started again, and motor 8 moves the second of the cells 7 into measurement position. Thereupon, the measurement is effected as described in connection with cell one, whereupon cell three is moved into measurement position. These steps go on until all six cells 7 are measured for the first time, i.e., until the first measurement cycle is completed.

The time between successive measurements is controlled by the computer program. This is effected in that the real-time-clock 71 via line 73 is loaded with a certain value. After expiration of this time value, the clock 71 via line 72 gives a pulse to computer 14, effecting a re-start of the program and thereby starting the next measurement. As mentioned, said time value is contained in the computer program, i.e., it is easy to change this time by changing the program.

After completing the first measurement cycle, the cell-changing device is returned to its starting position by means of motor 8. The time interval between the starting of the last measurement of the first cycle and the first measurement of the second cycle is also controlled by means of said real-time-clock 71. In the second cycle, the optimum amplification setting for each cell is no longer calculated but is taken from the storage of the computer 14. In this way, each sample is measured with the optimum setting of amplifier 10 corresponding to this sample without the operator having to change the adjustment of the apparatus. Again in this second cycle, the computer 14 calculates the mean and standard deviation values. The calculated mean value is stored and used as the second measurement point 47 shown in FIG. 1. The calculated standard deviation value is automatically compared to said value calculated and stored for the first measurement point. In each case, the greater value is stored while the smaller value is erased.

Figure 1:
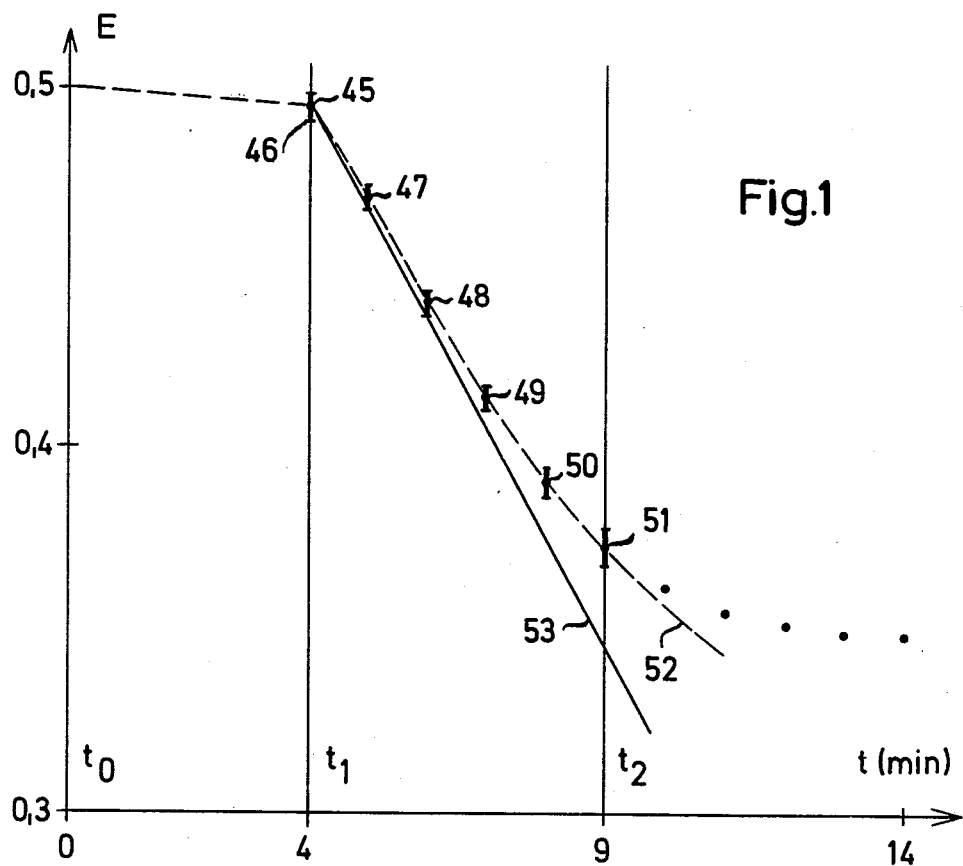
FIG. 1 is a graphical representation of a typical measurement curve, showing a relation between extinction E and time t.

In each subsequent measurement cycle, a similar measurement point is obtained for each of the cells 7, a succession of six being shown at 45 to 51 for one of the cells in FIG. 1, to cover observation until a time $t_2$. It will be recalled that each measurement point for a given sample cell is obtained from a plurality of individual measurements, the computer 14 in each case calculating and storing mean value and standard deviation.

After the end of all measurement cycles, the cell-changing motor 8 comes to a stop, and the computer calculates the enzyme activity for each sample using the stored values. For this purpose, according to the computer program and by computation, a regression curve is placed through the measurement points of each sample, as is indicated in FIG. 1 for the first sample. This curve is so calculated as a second-degree polynomial that the sum of the squares of the deviations at the individual measurement points is as small as possible.

In FIG. 1, the regression curve is marked 52, curve 52 being parabolic. A parabola has advantages over the straight regression lines previously used. Such a straight line is but a special case, for a given segment of the parabolic function; so that if all measurement points were observed to lie on a straight line or to be statistically distributed around it, the generalized parabola is equal to the task. However, if the change in extinction per unit of time is not constant, as is true in particular with high enzyme activities, a segment of the parabola is more representative of the true course than is a straight line.

The computer 14 determines automatically according to the program the direction of the tangent to the curve 52, for instance at the first or at the second measurement point. This tangent is designated 53 in FIG. 1, for the case of point 45. Since the course of the curve over the entire period of examination (points 45 to 51) is utilized for the determination of the tangent 53, the slope thus determined is substantially more accurate than the slope of a straight regression line which might otherwise have been drawn for instance only through the measurement points 45–48.

From the slope of the tangent 53, the computer 14 directly computes the enzyme activity sought, using said multiplication factor contained in the program and shown to be there by the lighting up of push button 64; it then prints out the calculated value of the enzyme activity of each sample via the printer 16. At the same time, an overall measurement error is calculated by the computer from the error in fit of the measurement points to the regression curve 52, the stored standard deviations, and the local curvature of the curve 52. This calculated value is printed together with the value of the enzyme activity, so that the new apparatus gives an objectively correct indication of error for each measurement point.

After completion of the described calculation process and the printing out of the measured values (at printer 16), the program of computer 14 goes back to its starting point, and the push button 66 lights up again, indicating that the apparatus is ready to measure the next samples.

By means of the push-buttons 68 shown in FIG. 2, the operator can select one of the cells 7, e.g., for testing the calibration of the apparatus.

Since the enzyme activity is given by the initial velocity of the enzyme-catalyzed reaction, only the measurement points 45 to 51 in FIG. 1, lying in the time interval $t_1 - t_2$, are used for the calculation of the enzyme activity value. The time interval $t_0 - t_1$ is reserved for any prior reaction and may be manually adjustable by pressing push button 66 at the time $t_1$ indicated by a clock which is started when the prior reaction starts at $t_0$. The time interval $t_0 - t_1$ may also be contained in the program of computer 14 which loads the real-time-clock 71 with the corresponding value when the button 66 is pressed and the prior reaction starts.

Despite its exceptionally high performance, the new apparatus is extremely simple to operate since the operator need merely depress a few push buttons which are provided with clear text and read the program in.

What is claimed is:

1. The method of determining enzyme activity in a given sample by plural light-extinction measurements on the sample employing electronic digital calculating apparatus which comprises performing a predetermined relatively rapid sequence of plural extinction measurements at a first point in time, repeating said relatively rapid sequence of measurements at second and succeeding relatively greatly spaced points in time, computing via said digital calculating apparatus the mean value to establish a measurement point for the plural measurements of each such rapid sequence, establishing a regression curve through the said measurement points, taking the tangent of said curve at a particular point in time, and calculating from the slope of this tangent the enzyme activity sought.

2. The method of claim 1, in which for each measuring point the mean value and the standard deviation are calculated and in which an overall measurement-error is calculated via said digital calculating apparatus from the deviation of said regression curve from the measurement points, said standard deviation and the curvature of the regression curve.

3. The method as in claim 2 wherein said measurement-error computing step includes the step of determining the square of the difference of the mean value at a measuring point and the value of said established regression curve at said measuring point.

4. The method of determining enzyme activity in a given sample by plural light-extinction measurements on the sample, which comprises performing a predetermined relatively rapid sequence of plural extinction measurements at a first point in time, repeating said relatively rapid sequence of measurements at second and succeeding relatively greatly spaced points in time, computing the mean value to establish a measurement point for the plural measurements of each such rapid sequence, establishing a regression curve through the said measurement points, taking the tangent of said curve at a particular point in time, and calculating from the slope of this tangent the enzyme activity sought in which enzyme activity of each of a plurality of cell-supported samples is measured, by indexing such cells successively into measurement position for the said first-point sequence of measurements on all samples prior to performing the second-point sequence of measurements on all samples, whereby the plural time-spaced sequences of one sample are time-interlaced with the corresponding time-spaced sequences of another sample.

5. The method of determining enzyme activity in a given sample by plural light-extinction measurements on the sample, which comprises performing a predetermined relatively rapid sequence of plural extinction measurements at a first point in time, repeating said relatively rapid sequence of measurements at second and succeeding relatively greatly spaced points in time, computing the mean value to establish a measurement point for the plural measurements of each such rapid sequence, establishing a regression curve through the said measurement points, taking the tangent of said curve at a particular point in time and calculating from the slope of this tangent the enzyme activity sought in which enzyme activity of each of a plurality of cell-supported samples is measured, by indexing such cells successively into measurement position for the said first-point sequence of measurements on all samples prior to performing the second-point sequence of measurements on all samples, whereby the plural time-spaced sequences of one sample are time-interlaced with the corresponding time-spaced sequences of another sample, in which the light-extinction measurements include photometrically and adjustably variable amplification of the electric signal, generating and separately storing an optimum amplification level uniquely applicable to each sample observed for the first point-in-time measurement applicable thereto, and synchronously commutating the respective stored levels to correspondingly adjust the amplification level used for optimal measurement of each sample for each of the succeeding points of time at which its light-extinction is measured.

6. The method of determining enzyme activity in a given sample by plural light-extinction measurements on the sample, which comprises performing a predetermined relatively rapid sequence of plural extinction measurements at a first point in time, repeating said relatively rapid sequence of measurements at second and succeeding relatively greatly spaced points in time, computing the mean value to establish a measurement point for the plural measurements of each such rapid sequence, establishing a regression curve through the said measurement points, taking the tangent of said curve at a particular point in time, and calculating from the slope of this tangent the enzyme activity sought, in which clock-pulse signals are used to determine precisely-spaced like periods of time between said measurement points.

7. The method of determining enzyme activity in a given sample by plural light-extinction measurements on the sample, which comprises performing a predetermined relatively rapid sequence of plural extinction measurements at a first point in time, repeating said relatively rapid sequence of measurements at second and succeeding relatively greatly spaced points in time, computing the mean value to establish a measurement point for the plural measurements of each such rapid sequence, establishing a regression curve through the said measurement points, taking the tangent of said curve at a particular point in time, and calculating from the slope of this tangent the enzyme activity sought, in which the regression curve is selected as a second-degree polynomial.

8. Apparatus for light-extinction measurement of enzyme activity in a sample, comprising a light source, photometer means spaced from and oriented for electrical response to light from said source, sample-supporting means interposed between said source and photometer means, analog-digital converter means connected to the electrical output of said photometer means, computer means connected to control a predetermined rapid sequence of measurements at each of a plurality of spaced points in time, said converter means being connected to said computer means, and said computer means including means for computing and storing the mean value for the collective measurements of each such sequence and for computing the enzyme activity using said stored measurement values.

9. Apparatus according to claim 8, in which said computer means are connected to a real-time-clock for timing the sequence of said measurements.

10. Apparatus according to claim 8, in which said photometer means includes variable-gain amplifier means, said computer including means for calculating from measured output for measurements at a first point in time an optimum gain setting for said amplifier means, means for storing a value corresponding to said optimum setting, and means establishing a control connection from said storage means to reset said amplifier gain for measurements at a later point in time based on the stored value.

11. Apparatus according to claim 10, in which the variable gain of said amplifier means comprises a plurality of discrete, purely digitally selectable amplification stages.

12. Apparatus according to claim 8, characterized by the fact that said photometer means includes coded filters whose code numbers are interrogated by the computer.

13. Apparatus as in claim 8, wherein said computer means includes means for determining the standard deviation at said spaced points in time, and means for fitting a curve through said mean and deviation measurements.

14. Apparatus as in claim 13 wherein said computer means further comprises means for determining the derivative of said curve produced by said curve fitting portion thereof.

15. In combination in enzyme activity determining means, light source and light detector means for determining relative light transmissivity of a sample disposed therebetween, means for repetitively sampling the output of said detector means at spaced points in time relatively large in comparison to the inter-sample interval for any said point in time, computer means for receiving said sampled detector output signals, said computer means including means for determining statistical light transmissivity for the samples at any point in time, means for fitting a curve to said statistical properties determined by said means therefor, and means for determining the derivative of said curve determined by said curve fitting means.

16. A combination as in claim 15 wherein said statistical property determining means includes mean value determining means.

17. A combination as in claim 16 wherein said curve fitting means includes means for fitting a second degree polynomial curve to said mean values.

* * * * *

UNITED STATES PATENT OFFICE
CERTIFICATE OF CORRECTION

Patent No. 4,055,752      Dated October 25, 1977

Inventor(s) Walter Kappe et al.

It is certified that error appears in the above-identified patent and that said Letters Patent are hereby corrected as shown below:

Column 10, Claim 15, line 57, insert -- properties -- before "for" .

Signed and Sealed this

Fourteenth Day of February 1978

[SEAL]

Attest:

RUTH C. MASON
*Attesting Officer*

LUTRELLE F. PARKER
*Acting Commissioner of Patents and Trademarks*